United States Patent
Thiele et al.

(10) Patent No.: US 6,517,491 B1
(45) Date of Patent: Feb. 11, 2003

(54) TRANSDUCER WITH SPATIAL SENSOR

(75) Inventors: Karl E Thiele, Andover, MA (US); Showna Hsu-Hwa Chang, Somerville, MA (US)

(73) Assignee: Koninklijke Philips Electronics N.V, Eindhoven (NL)

( * ) Notice: Subject to any disclaimer, the term of this patent is extended or adjusted under 35 U.S.C. 154(b) by 37 days.

(21) Appl. No.: 09/702,328

(22) Filed: Oct. 31, 2000

(51) Int. Cl.$^7$ ................................................ A61B 8/14
(52) U.S. Cl. ..................................................... 600/459
(58) Field of Search .................. 600/407, 424–427, 600/437–472; 73/625, 626

(56) References Cited

U.S. PATENT DOCUMENTS

| | | | |
|---|---|---|---|
| 4,463,763 A | | 8/1984 | Koyano et al. |
| 4,849,692 A | | 7/1989 | Blood |
| 4,945,305 A | | 7/1990 | Blood |
| 5,337,149 A | | 8/1994 | Kozah et al. |
| 5,529,070 A | | 6/1996 | Augustine et al. |
| 5,538,004 A | | 7/1996 | Bamber |
| 5,600,330 A | | 2/1997 | Blood |
| 5,742,394 A | | 4/1998 | Hansen |
| 5,744,953 A | | 4/1998 | Hansen |
| 5,767,669 A | | 6/1998 | Hansen et al. |
| 5,771,896 A | * | 6/1998 | Sliwa et al. ................. 600/462 |
| 5,831,260 A | | 11/1998 | Hansen |
| 5,953,683 A | | 9/1999 | Hansen et al. |
| 5,957,844 A | | 9/1999 | Dekel et al. |
| 6,080,108 A | | 6/2000 | Dunham |
| 6,266,550 B1 | * | 7/2001 | Selmon et al. ............... 600/407 |

OTHER PUBLICATIONS

"MiniBIRD Position and Orientation Measurement System" Installation and Operation Guide, Feb. 10, 1997; Ascension Technology Corporation; 129 pages.

"OBGYN.net Conference Coverage", San Franciso, CA; Apr. 2000; obtained from URL: http://www.obgyn.net/avtranscripts/aium2000$_{13}$shy.htm—printed Sep. 20, 2000.

"3D Ultrasound—Acquisition Methods Details"; obtained from URL: http://www.lifeimage.com/techdeta.htm—printed Jun. 30, 2000.

"Flock of Bird", Ascension Technology Corporation; obtained from URL: http://www.ascension-tech.com/products/flockobirds/flockofbirds.htm; printed on Jun. 27, 2000.

"Microtool Opens 3D Window Into The Human Body", by Cleopartra Alfenito; Ascension Technology Corporation; obtained from URL: http://www.ascension-tech.com/inthenews/microtool1.htm.

"3D Ultrasound Scanhead Tracking" by Cleopatra Alfenito; Ascension Technology Corporation, obtained from URl: http://www.ascension-tech.com/inthenews/soundbytes.htm, printed on Jun. 29, 2000.

"The Method: 3D Ultrasound Sensor Supported Acquisition And Postprocessing", EchoTech 3D Imaging Systems, Inc.; obtained from URL: http://www.3dechotech.com/framesets/pages/Method.htm; printed on Jun. 29, 2000.

"3D Freehand Ultrasound: Reconstruction And Spatial Compounding" by Robert Nicolas Rohling, Churchill College, Sep. 1998.

"Correcting Motion–Induced Registration Errors in 3D Ultrasound Images", by Rohling, et al., Proc. British Machine Vision Conference 1996, vol. 2, pp. 645–654.

(List continued on next page.)

*Primary Examiner*—Marvin M. Lateef
*Assistant Examiner*—Ali M. Imam

(57) ABSTRACT

An ultrasound system comprising an ultrasound unit and a transducer. The transducer including a transducer housing integrating at least one element integrated and a first spatial locator unit. The ultrasound unit includes an imaging unit that receives an echo signal from the at least one element of the transducer and outputs echo data. A second spatial locator unit, in communication with the first spatial locator unit, is integrated with the ultrasound unit. The second spatial locator unit enables the determination of a location of the transducer housing.

11 Claims, 3 Drawing Sheets

OTHER PUBLICATIONS

"3D Ultrasound Imaging: Optimal Volumetric Reconstruction", by R.N. Rohling; May 15, 1996; Cambridge University Engineering Department; pp. 1–34.

"Automatic Registration Of 3D Ultrasound Images"; by Rohling, et al; May 1997, Cambridge University Engineering Department; pp. 1–23.

"Spatial Compounding Of 3D Ultrasound Images", by Rohling, et al.; Oct., 1996; Cambridge University Engineering Department; pp. 1–27.

"Automatic Calibration For 3D Free Hand Ultrasound", by Prager, et al.; Sep., 1997; Cambridge University Engineering Department; pp. 1–27.

Issues In 3D Free Hand MedicalUltrasound Imaging; by Rohling, et al.; Jan., 1996; Cambridge University Engineering Department; pp. 1–28.

"Radial Basis Function Interpolation for 3D Ultrasound"; by Rohling, et al.; Jul., 1998; Cambridge University Engineering Department; pp. 1–27.

* cited by examiner

TRANSDUCER WITH SPATIAL SENSOR

BACKGROUND OF THE INVENTION

The present invention relates to an integrated spatial sensor and transducer, and in particular to a housing combining a transducer and spatial sensor.

Ultrasound has become a popular technique for the imaging and measuring of internal organs and anatomy. Ultrasound has several advantages over MRI and CT scanning: ultrasound is real-time, non-invasive, non-radiative, and relatively less expensive to buy and maintain compared to MRI and CT equipment. As with most medical technology, ultrasound systems are evolving to take advantage of new technologies and in response to the ever-increasing demands of medical professionals. One of the most requested features on ultrasound systems is the ability to present an image having the appearance of 3-D. Such an image is produced from a 3-D matrix of data. Generally, three dimensional data is presented in one of two forms: a surface scanned structure or a volume scanned structure. Either structure is formed by isonifying a volume and rendering the data to produce a 2-D image showing a 3-D object (referred to herein as a 3-D image).

Currently, there are two different methods for obtaining scan data in preparation for rendering a 3-D surface. The first method involves the use of a 1-D transducer which typically uses a linear array of elements to produce a 1-D slice of data. Alternatively, a single element transducer can be mechanically oscillated. After each slice is obtained, the sonographer (or more generically "user") moves the transducer to obtain another slice. Software is then used to stitch together a volume data set.

The second method involves the use of a two-dimensional transducer array to isonify a volume. In this method, two broad categories exist. Some systems use a so-called 1.5-D array, which comprises several rows of elements. A 1.5-D array can be conceptually thought of as a stack of convention 1-D arrays, each independently steerable along the azimuth. A 1.5-D array is not steerable in the elevation direction. A true 2-D array is a matrix of elements (and is sometimes referred to as a "matrix array") which acts as a unified whole and is steerable in the elevation direction. True 2-D array transducers are believed to be capable of producing a three dimensional volume of data without requiring significant operator involvement. At the present time, true 2-D transducers are largely experimental and very expensive, but the results have exceeded expectations. However, it has been determined that the response of tissue structures perpendicular to the face of the 2-D array is attenuated, such that some of the image produced by echoes off of such tissue structures is faint or nonexistent.

For the present, the first method of obtaining a plurality of data slices and stitching them together to form a volume data set is the preferred method of obtaining a 3-D image.

Freehand imaging is a method to develop 3-D images in which the sonographer moves a 1-D array across a patient "freehand" and a specialized graphic processor attempts to warp together a 3-D image. One innovation that has greatly improved the image quality of 3-D images produced using the freehand method is the use location sensors externally mounted on a 1-D ultrasound transducer to register the spatial location and orientation with respect to translation and angulation of acquired ultrasound images. This method is typically referred to as the calibrated freehand method. To develop 3-D images, each 2-D image pixel is mapped to a physical location in the patient's coordinate set. Data sets obtained from the scan are transformed into a Cartesian coordinate system to enable visualization similar to that provided by CTs or MRIs. Typically, a graphics workstation, such as those offered by SILICON GRAPHICS, assists with real-time visualization. Further, animation can be employed to perform rotations and zooming or to create a "cine-loop" display. Using such techniques, reconstructed 3-D images of the heart, blood vessels, stomach and other organs can be developed. Essentially, the 2-D image slices or "planes" that stand-alone ultrasound provides are "pasted" together to provide a 3-D data set which can be rendered and displayed on a 2-D monitor. The 3-D data set is amenable to interaction and manipulation, and can be shared for remote consults via download or stored digitally.

Ascension Technology Corporation produces several models of magnetic location sensors under their FLOCK OF BIRDS™ line that are suitable for use with the calibrated freehand method. For example, the DC-pulsed magnetically tracked mini-sensor (18 mm×8 mm×8 mm) of the mini-BIRD™ system measures 6 degrees of freedom when mounted on an ultrasound probe and are suitable for internal or external anatomical explorations. The pcBIRD™ is a 6 degree of freedom tracker on a PC card that dedicates a separate processor for each receiver. It measures the location and orientation of a small receiver referenced to a magnetic transmitter. The electronics board plugs into the ISA slot of any PC computer.

FIG. 1 is a block diagram of a known ultrasound imaging system 100 configured for freehand scanning. An ultrasound unit 110 generally comprises a housing (such as a cart) supporting an imaging unit that includes transmission and reception circuits (including for example a beamformer) along with an image processing unit including display circuits. A transducer 112, connected to the ultrasound unit 110, outputs and receives ultrasound signals under the control of the imaging unit so as to scan a patient 114 in a known manner.

The ultrasound imaging system 100 is configured for use with the miniBIRD system from ASCENSION TECHNOLOGY CORPORATION. Like all known freehand imaging systems, Ascension Technologies' applications call for the external attachment of a sensor to a transducer. A transmitter 116 is positioned in the vicinity of the patient 114, typically in connection with a bed or table upon which the patient 114 rests. A receiver 118, affixed to the surface of the transducer 112, receives a pulsed DC magnetic field transmitted by the transmitter 116. From measured magnetic field characteristics, the receiver 118 computes its location and orientation and makes this information available to a host computer 120 via a controller 122. The controller 122 synchronizes operation of the transmitter 116 and receiver 112 under the direction of the host computer 120.

The host computer 120 is also in communication with the ultrasound unit 110. The host computer 120, using location information from the receiver 118 and ultrasound image data from the ultrasound unit 110, tags individual frames of ultrasound image data with location information and "stitches" together the various frames, using known algorithms, to produce 3-D images. For example, EchoTech 3-D Imaging Systems Inc. of Lafayette, Colo. produces systems that are capable of interfacing with the miniBIRD system and various ultrasound systems to produce real-time (or more accurately near real-time) 3-D images.

Systems similar to the one shown in FIG. 1 have several drawbacks. The first, and perhaps the most dangerous, is that such systems require a number of separate devices and a plurality of cables to connect the devices. For example, the transducer 112 has two cables extending therefrom, one going to the controller 122 and one going to the ultrasound unit 110. Additionally, the controller 122, transmitter 116 and host computer 120 all have various cables extending therefrom. In the already crowded medical environment, such clutter can lead to disaster, torn cables, shattered equipment, and perhaps even injury to the patient or attending professionals. A second problem arises due to the external attachment of the receiver 118, that of indeterminate calibration. Each time the receiver 118 is re-attached to the transducer 112, a calibration procedure should be initiated to determine the orientation between the transducer 112 and receiver 118. This orientation information is critical for accurate "stitching" in the host computer 120. As critical as this information is, there may be times when operators fail to perform such calibration, due to time constraints. Additionally, the method used to attach the receiver 118, i.e. velcro, glue, or straps, all have the potential to shift during use, causing artifacts in the stitched output.

The present inventors have recognized a need for a more accurate and user friendly calibrated freehand device. The present inventors have also invented new models of use for transducers (either 1-D or 2-D ) equipped with location sensing devices.

SUMMARY OF THE INVENTION

An ultrasound system comprising an ultrasound unit and a transducer. The transducer including a transducer housing integrating at least one element and a first spatial locator unit. The ultrasound unit includes an imaging unit that receives an echo signal from the at least one element of the transducer and outputs echo data. A second spatial locator unit, in communication with the first spatial locator unit, is integrated with the ultrasound unit. The second spatial locator unit in connection with the first spatial locator unit enables the determination of a location of the transducer housing.

The novel ultrasound system is particularly useful in producing 3-D images with 1-D arrays and improving the imaging quality of 3-D images by simplifying set-up, calibration and use of the ultrasound system. For example, the novel ultrasound system facilitates a method comprising the steps of isonifying a first volume from a first position, using a 2-D array of elements, in a first scanning operation; determining a relative location of the first position; receiving first echo data from the first scanning operation and relating the relative location of the first position to the first echo data; isonifying a second volume from a second position, using a 2-D array of elements, in a second scanning operation, the second volume overlapping at least a portion of the first volume; determining a relative location of the second position; receiving second echo data from the second scanning operation and relating the relative location of the second position to the second echo data; and creating a display of the at least a portion of the first volume using the first echo data and the second echo data.

As another example, the novel ultrasound system facilitates the automatic powering down of a transducer or system based on a location of a second spatial locator fixed relative to the ultrasound unit. Because the location of the second spatial locator is fixed, the location of the transducer relative to the ultrasound unit can easily be determined such that when the transducer is left lying around or returned to the ultrasound unit, power can automatically be shut off to the system or transducer. Of course the system could also be placed in a sleep mode based o n the location of the transducer.

BRIEF DESCRIPTION OF THE DRAWINGS

These and other objects and advantages of the invention will become apparent and more readily appreciated from the following description of the preferred embodiments, taken in conjunction with the accompanying drawings of which.

DESCRIPTION OF THE PREFERRED EMBODIMENTS

Figure 1:
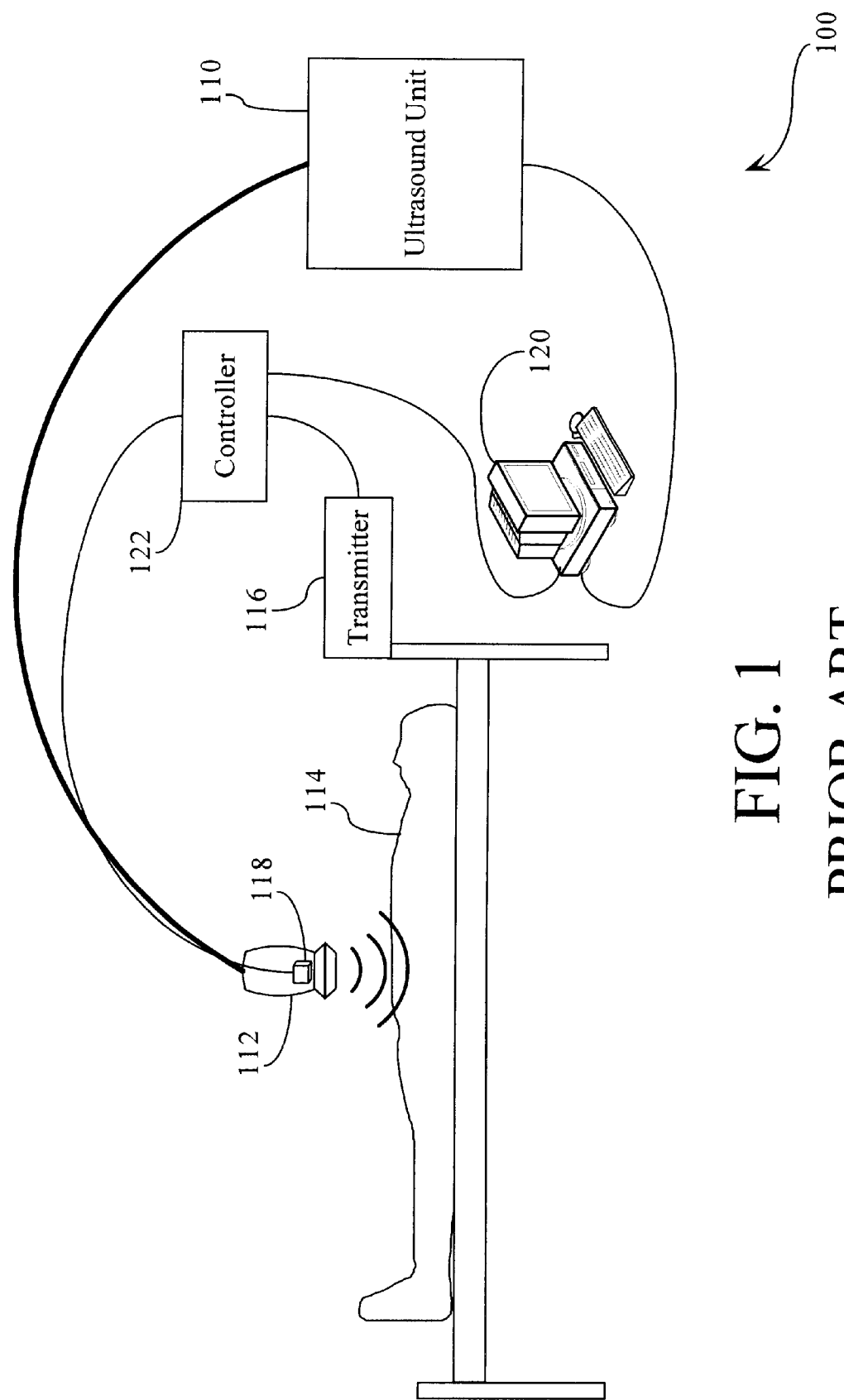
FIG. 1 is a block diagram of a known ultrasound system.

Reference will now be made in detail to the present preferred embodiments of the present invention, examples of which are illustrated in the accompanying drawings, wherein like reference numerals refer to like elements throughout.

The present invention provides an ultrasound system with a transducer integrating transducer element(s) with a spatial locator receiver along with an ultrasound unit integrated with a spatial locator transmitter and associated control circuitry. The term "transducer element" (or more simply "element") refers to a single transmission/reception element in a transducer regardless of construction, such as PZT or newer semiconductor based technology.

The apparatus set forth in the present application is preferably specifically constructed for the required purpose, i.e. ultrasound imaging, but the apparatus recited herein may be embodied by a general purpose computer or other network device selectively activated or reconfigured by routines stored in the computer and interfaced with the necessary ultrasound imaging equipment. The apparatus presented herein is not inherently related to any particular ultrasonic system, computer or other apparatus. In particular, various machines may be used with routines in accordance with the teachings herein, or it may prove more convenient to construct more specialized apparatus to perform the required method steps. In certain circumstances, when it is desirable that a piece of hardware possess certain characteristics, these characteristics are described more fully in the following text. The required structures for a variety of these machines may appear in the description given below. Machines which may be modified in accordance with the teachings of the present invention include those manufactured by such companies as AGILENT TECHNOLOGIES, PHILIPS MEDICAL SYSTEMS INTERNATIONAL, GE MEDICAL SYSTEMS, and SIEMANS MEDICAL SYSTEMS, as well as other manufacturers of ultrasound equipment.

With respect to the software described herein, those of ordinary skill in the art will recognize that there exists a variety of platforms and languages for creating software for performing the procedures outlined herein. Those of ordinary skill in the art also recognize that the choice of the exact platform and language is often dictated by the specifics of the actual system constructed, such that what may work for one type of system may not be efficient on another system.

Figure 2:
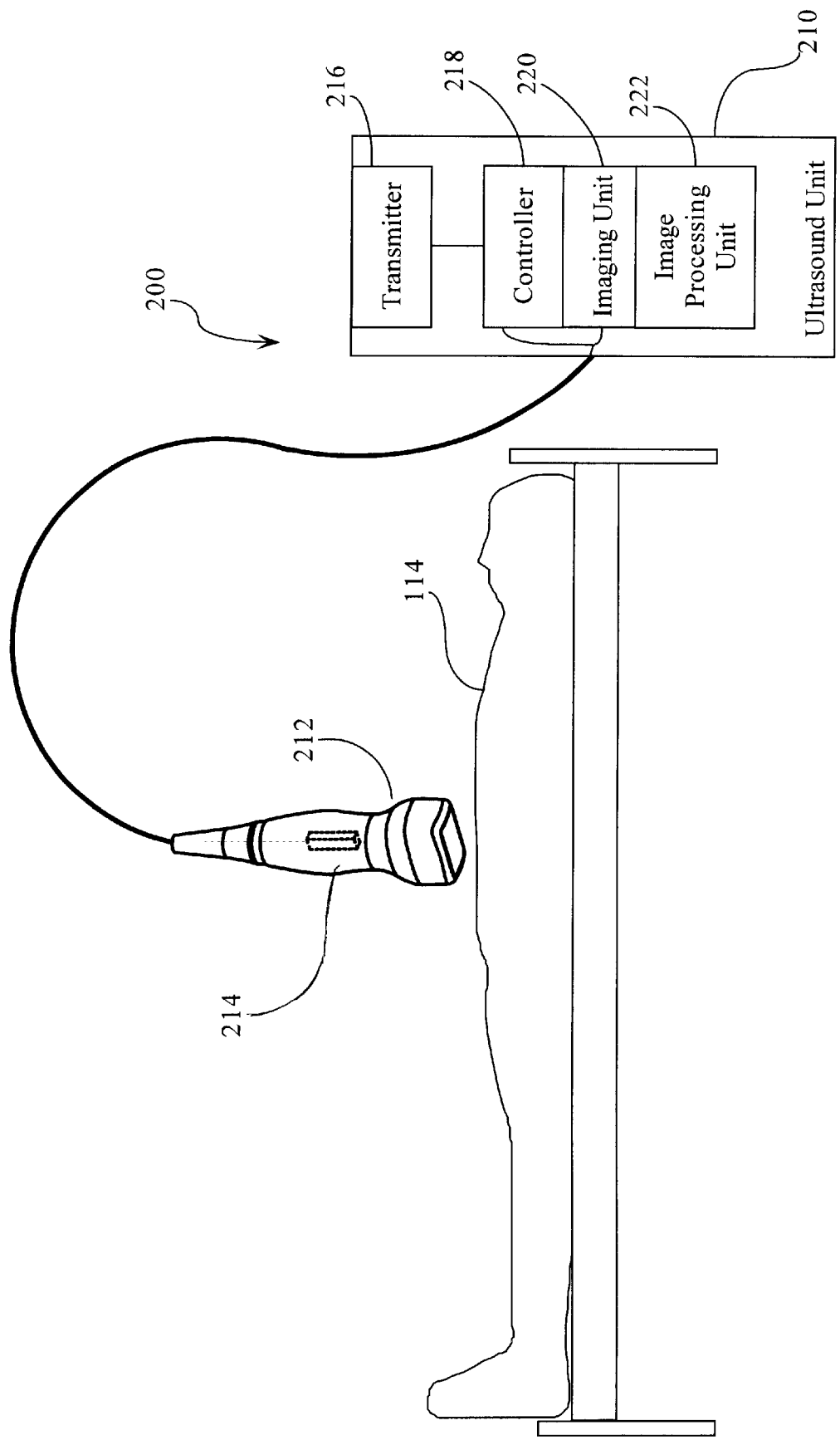
FIG. 2 is a block diagram of an ultrasound system in accordance with the preferred embodiment of the present invention.

FIG. 2 is a simplified block diagram of an ultrasound imaging system 200 in accordance with the preferred embodiment of the present invention. It will be appreciated by those of ordinary skill in the relevant arts that the ultrasound imaging system 200, as illustrated in FIG. 2, and the operation thereof as described hereinafter is intended to be generally representative such systems and that any particular system may differ significantly from that shown in FIG. 2, particularly in the details of construction and operation of such system. As such, the ultrasound imaging system 200 is to be regarded as illustrative and exemplary and not limiting as regards the invention described herein or the claims attached hereto.

The ultrasound imaging system 200 generally comprises an ultrasound unit 210 and a connected transducer 212. The transducer 212 comprises a housing integrating at least one element (not shown) and a spatial locator receiver (or simply "receiver") 214. The ultrasound unit 210 has integrated therein a spatial locator transmitter (or simply "transmitter") 216 and an associated controller 218. The ultrasound unit 210 is also provided with imaging unit 220, for controlling the transmission and receipt of ultrasound, and an image processing unit 222 for producing a display on a monitor (not shown). The image processing unit 222 contains routines, known to those of ordinary skill in the art, for stitching together and rendering a 3-D image. The transmitter 216 should be located in an upper portion of the ultrasound unit 210 so as to obtain a clear transmission to the receiver 214. As modern ultrasound units are often configured in a cart format, such mounting should not be a problem, such that the details thereof are omitted. During freehand imaging, a user moves the transducer 212 over a subject in controlled motion. The ultrasound unit 210 combines image data produced by the imaging unit 220 with location data produced by the controller 218 to produce a matrix of data suitable for rendering onto a monitor.

Figure 3:
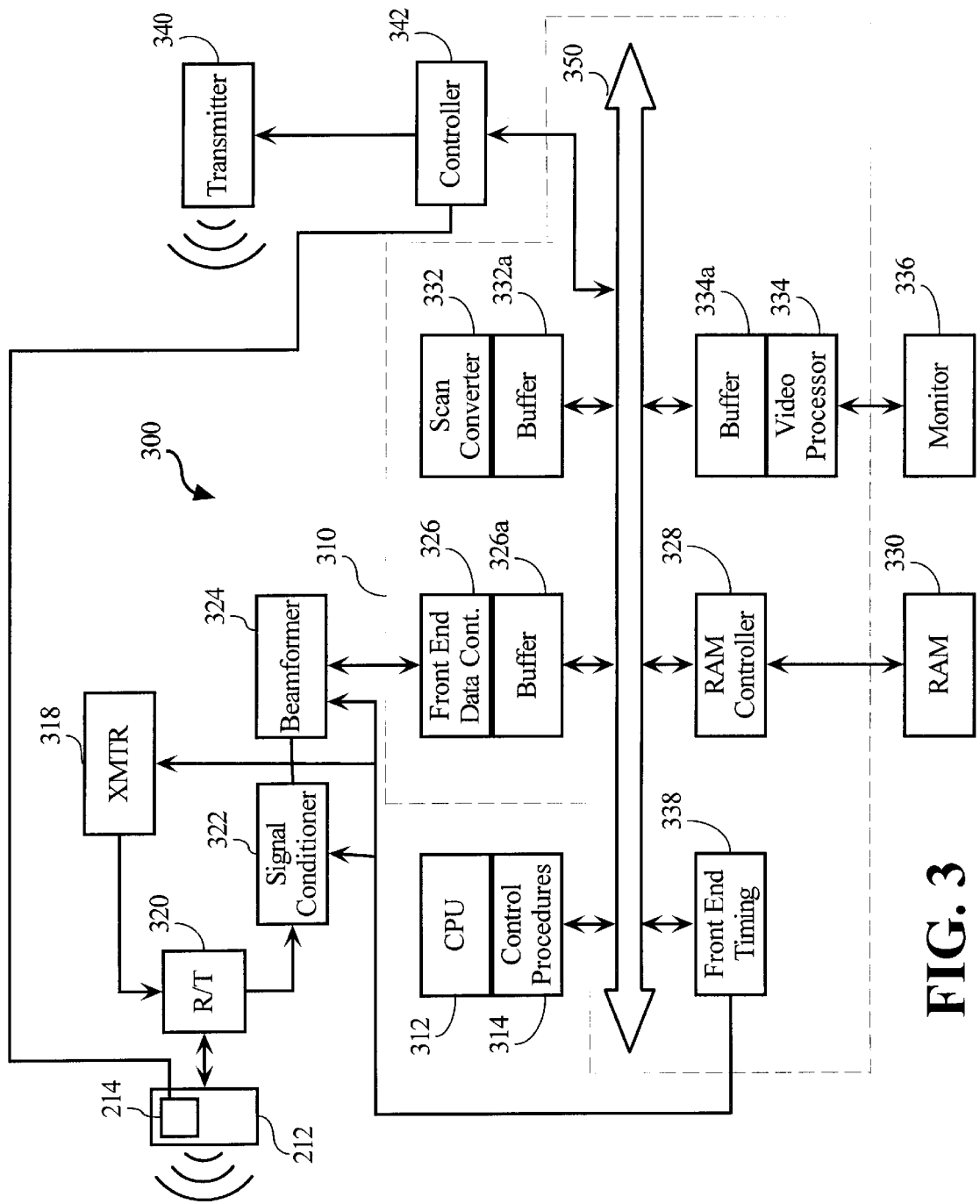
FIG. 3 is a block diagram of an ultrasound unit in accordance with the preferred embodiment of the present invention.

The ultrasound imaging system 200 greatly simplifies freehand imaging, by eliminating many of the calibration problems inherent in the prior art system and eliminating the attendant clutter of such prior art systems. The integration of stitching and rendering processes with known image processing functions is facilitated by the increasing use of general purpose processors and PC-like architectures in ultrasound systems. Alternatively, existing 2-D ultrasound systems can be updated with a channel link that strips data directly from a beamformer allowing scan conversion, stitching and rendering to be performed on a stand alone PC (which can be physically integrated with the ultrasound imaging system 200) Thus, the user could use the existing 2-D ultrasound system in its original modalities with out any impact whatsoever. When 3-D imaging is desired, the stripped data can be processed by the stand alone PC and displayed. On the other hand, use of ASICs to perform the stitching and rendering is possible. FIG. 3 shows an example of an ultrasound system that utilizes a newer architecture which can accommodate the necessary software imaging processes to perform stitching and rendering.

FIG. 3 is a block diagram of an ultrasound unit 300 in accordance with the preferred embodiment of the present invention. It will be appreciated by those of ordinary skill in the relevant arts that the ultrasound imaging system 300, as illustrated in FIG. 3, and the operation thereof as described hereinafter is intended to be generally representative such systems and that any particular system may differ significantly from that shown in FIG. 3, particularly in the details of construction and operation of such system. As such, the ultrasound imaging system 300 is to be regarded as illustrative and exemplary and not limiting as regards the invention described herein or the claims attached hereto.

The ultrasound imaging system shown in FIG. 3 is configured for the use of pulse generator circuits, but could be equally configured for arbitrary waveform operation. The ultrasound system 300 utilizes a centralized architecture suitable for the incorporation of standard personal computer ("PC") type components.

The ultrasound system 300 includes a transducer 214 which, in a known manner, scans an ultrasound beam, based on a signal from a transmitter 318, through an angle. Backscattered signals, i.e. echoes, are sensed by the transducer 214 and fed, through a received/transmit switch 320, to a signal conditioner 322 and, in turn, to a beamformer 324. The transducer 214 includes elements, preferably configured as a steerable one-dimensional array. The signal conditioner 322 receives the backscattered ultrasound signals and conditions those signals by amplification and forming circuitry prior to their being fed to the beamformer 324. Within the beamformer 324, the ultrasound signals are converted to digital values and are configured into "lines" of digital data values in accordance with amplitudes of the backscattered signals from points along an azimuth of the ultrasound beam.

The beamformer 324 feeds the digital values to an application specific integrated circuit (ASIC) 310 which incorporates the principal processing modules required to convert the digital values into a form more conducive to video display for feed to a display 336.

A front end data controller 326, receives the lines of digital data values from the beamformer 324 and buffers each line, as received, in an area of a buffer 326a. After accumulating a line of digital data values, the front end data controller 326 dispatches an interrupt signal, via a bus 350, to a shared central processing unit (CPU) 312, such as a MOTOROLA PowerPC. The CPU 312 executes control procedures 314 including procedures that are operative to enable individual, asynchronous operation of each of the processing modules within the ASIC 310. More particularly, upon receiving the interrupt signal, the CPU 312 causes a line of digital data values data residing in the buffer 326a to be fed to a random access memory (RAM) controller 328 for storage in a random access memory (RAM) 330 which constitutes a unified, shared memory. RAM 330 also stores instructions and data for the CPU 312, lines of digital data values and data being transferred between individual modules in the ASIC 330, all under control of the RAM controller 328.

In accordance with a preferred embodiment of the present invention the transducer 212 incorporates a receiver 214 that operates in connection with a transmitter 340 to generate location information. The location information is supplied to (or created by) a controller 342 which outputs location data in a known manner. The location data is stored (under the control of the CPU 312) in the RAM 330 in conjunction with the storage of the lines of digital data value.

A front end timing controller 338 is controlled by one of the control procedures 314 to output timing signals to the transmitter 316, the signal conditioner 322, the beamformer 324, and the controller 342 so as to synchronize their operations with the operations of the modules within ASIC 310. The front end timing controller 338 further issues timing signals which control the operation of the bus 350 and various other functions within the ASIC 310.

As aforesaid, the control procedures 314 configures the CPU 312 to enable the front end data controller 326 to move the lines of digital data values and location information into the RAM controller 328 where they are then stored in RAM 330. Since the CPU 312 controls the transfer of lines of digital data values, it senses when an entire image frame has been stored in RAM 330. At this point, the CPU 312, as configured by the control procedures 314. recognizes that data is now available for operation by a scan converter 332, at which point, the CPU 312 notifies the scan converter 332 that it can access the frame of data from RAM 330 for processing.

To access the data in RAM 330 (via RAM controller 328), the scan converter 332 interrupts the CPU 312 to request a line of the data frame from RAM 330. Such data is then transferred to a buffer 332a of the scan converter 332, and is transformed into data based on an X-Y coordinate system. When this data is coupled with the location data from the controller 342 a matrix of data in an X-Y-Z coordinate system is created. A four (4) dimensional matrix can be used for 4-D (X-Y-Z-time) data. This process is repeated for each subsequent line of digital data values of the image frame from RAM 330. The resulting processed data is returned, via the RAM controller 328, into RAM 330 as display data. The display data is stored separately from the data produced by the beamformer 324. The CPU 312 and the control procedures 314, via the interrupt procedure described above, sense the completion of the operation of the scan converter 332. A video processor 334, such as the MITSUBISHI VOLUMEPRO series of cards, interrupts the CPU 312 which responds by causing a feed of lines of video data from the RAM 330 into a buffer 334a associated with the video controller 334. The video processor 334 uses the video data to render an image for display on the monitor 336.

The configuration shown in FIGS. 2 and 3 is also particularly useful when the transducer contains a 2-D array capable of scanning a volume without requiring motion of the transducer 212 as in the freehand method. The data produced by such 2-D arrays typically suffers from attenuated signals produced by tissue structures perpendicular to the plane of the 2-D array. Using the system of the present invention, two volume data sets can be produced, the second at some angle (preferably 90 degrees) from the first. Because the controller 342 can provide location information for the first and second scans, the two volume data sets can be placed in the same space and compounded (such as by averaging) to produce a superior image. It is noted that volumes produced by the freehand method may also benefit from this innovation.

To implement, the scan converter would be directed to place data from the first scan in a first matrix (a three axis matrix for static images and a four axis matrix for motion images) and data from the second scan in a second matrix having a similar structure to the first matrix. Motion images would have to be temporally adjusted, based for example on an ECG signal, while static images would preferably be triggered to be taken from the same portion of the ECG cycle. A subsequent process, perhaps performed by the CPU 312 under the control of a suitable control procedure 314, would combine the two matrixes. Such a combination can be performed using averages or some other form of compounding. For example, the two values for any given space would be compared and a third value, such as the greater of the two values, could be used as the final value.

Although a few preferred embodiments of the present invention have been shown and described, it would be appreciated by those skilled in the art that changes may be made in these embodiments without departing from the principles and spirit of the invention, the scope of which is defined in the claims and their equivalents.

For example, in the highly regulated ultrasound field, it is always desirable to automatically shut off power to a transducer or the entire system when the transducer is determined not to be in use. The controller 218 could be periodically polled to determine if the transducer 212 has not been moved for a period of time. Once this time period has been exceeded, for example, the power to the transducer 212 can be shut off, the entire system can be shut down or a sleep mode can be activated. Further, since the location of the transmitter 216 is fixed with respect to the ultrasound unit 210 it can be determined if the transducer 212 has been returned to the ultrasound unit 210 upon which time the power to the transducer 212 can be shut off.

What is claimed is:

1. An ultrasound system comprising:
   a transducer including:
     a transducer housing;
     at least one element integrated in the transducer housing; and
     a first spatial locator unit integrated in the transducer housing; and
   an ultrasound unit including:
     an imaging unit that receives an echo signal from the at least one element of the transducer and outputs echo data; and
     a second spatial locator unit, in communication with the first spatial locator unit, that enables the determination of a location of the transducer housing.

2. An ultrasound system, as set forth in claim 1 wherein the ultrasound unit further includes:
   a cart that supports the imaging unit and the second spatial locator unit.

3. An ultrasound system, as set forth in claim 2, wherein the ultrasound unit further includes:
   a controller connected to the first spatial locator unit and the second spatial locator unit that causes the second spatial locator unit to output a signal to be received by the first spatial locator unit and output a signal to the controller indicative of a location of the first spatial locator with respect to the second spatial locator; and
   a shut off process that shuts down power to the transducer based on a location of the transducer.

4. An ultrasound system, as set forth in claim 3, wherein the shut off process shuts down power to the transducer when the location of the transducer remains constant for a predetermined period of time.

5. An ultrasound system, as set forth in claim 1 wherein the ultrasound unit further includes a controller connected to the first spatial locator unit and the second spatial locator unit that causes the second spatial locator unit to output a signal to be received by the first spatial locator unit and output a signal to the controller indicative of a location of the first spatial locator with respect to the second spatial locator.

6. An ultrasound system, as set forth in claim 5 wherein the controller outputs a signal indicating the location of the second spatial locator and the ultrasound unit further includes: a image processing unit that receives the echo data from the imaging unit and the location of the second spatial locator unit from the controller and creates a matrix of data.

7. An ultrasound system, as set forth in claim 6 wherein the at least one element of the transducer comprises a plurality of elements arranged in a 2-D array and the imaging unit of the ultrasound unit controls the 2-D array of elements to obtain echo data from a volume.

8. An ultrasound system, as set forth in claim 7, wherein the image processing unit creates a first matrix of data representing a first volume as imaged from a first location of the transducer and a second matrix of data representing a second volume, which overlaps at least a portion of the first volume, as imaged from a second location of the transducer.

9. An ultrasound system, as set forth in claim 8, wherein the image processing unit uses the first matrix of data and the second matrix of data to generate a third matrix of data which is used for rendering and display.

10. A method of imaging comprising:

isonifying a first volume from a first position, using a 2-D array of elements, in a first scanning operation;

determining a relative location of the first position;

receiving first echo data from the first scanning operation and relating the relative location of the first position to the first echo data;

isonifying a second volume from a second position, using a 2-D array of elements, in a second scanning operation, the second volume overlapping at least a portion of the first volume;

determining a relative location of the second position;

receiving second echo data from the second scanning operation and relating the relative location of the second position to the second echo data; and creating a display of the at least a portion of the first volume using the first echo data and the second echo data.

11. A method, as set forth in claim 10, wherein the step of creating a display comprises compounding the first echo data with the second echo data.

* * * * *